United States Patent
Naides et al.

(10) Patent No.: US 11,768,202 B2
(45) Date of Patent: Sep. 26, 2023

(54) METHOD OF DETECTING ANTI-RI IN A SUBJECT WITH A PREVIOUS STREPTOCOCCAL INFECTION

(71) Applicant: Quest Diagnostics Investments LLC, Secaucus, NJ (US)

(72) Inventors: Stanley J. Naides, Dana Point, CA (US); Joanna Popov, Ladera Ranch, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 327 days.

(21) Appl. No.: 16/209,100

(22) Filed: Dec. 4, 2018

(65) Prior Publication Data

US 2019/0107536 A1    Apr. 11, 2019

Related U.S. Application Data

(63) Continuation of application No. 15/157,949, filed on May 18, 2016, now abandoned, which is a continuation of application No. 13/718,288, filed on Dec. 18, 2012, now abandoned.

(60) Provisional application No. 61/579,546, filed on Dec. 22, 2011.

(51) Int. Cl.
*G01N 33/564* (2006.01)
*G01N 33/68* (2006.01)
*G01N 33/569* (2006.01)

(52) U.S. Cl.
CPC ..... *G01N 33/564* (2013.01); *G01N 33/56944* (2013.01); *G01N 33/6854* (2013.01); *G01N 2333/315* (2013.01); *G01N 2469/20* (2013.01); *G01N 2800/38* (2013.01)

(58) Field of Classification Search
None
See application file for complete search history.

(56) References Cited

PUBLICATIONS

Dale et al (British Journal of Psychiatry ;2005, 187314-319.*
Hahn et al (Am.Fam Physician 2005;71:1949-54).*
Kiessling et al Pediatrics, 1993;vol. 92, Issue: 1, pp. 39-43.*
Gause et al (Journal of neuroimmunologey 2009;217,pp. 188-124.*
Walker et al., Differential Diagnosis of Chorea, Curr. Neurol. Neurosci. Rep, 11, (2011), p. 385-395 (Year: 2011).*
Kiryluk et al., Acute chorea and bilateral basal ganglia lesions in a hemodialysis patient, Kidney International, 73, (2008), p. 1087-1091 (Year: 2008).*
van Toorn et al., Distinguishing PANDAS from Sydenham's chorea: case report and review of the literature, European Journal of Paediatric Neurology, 8, (2004), p. 211-216 (Year: 2004).*
Black et al., "Serologic survey of adult patients with obsessive-compulsive disorder for neuron-specific and other autoantibodies," Psychiatry Research, vol. 81, pp. 371-380, 1998.
Beckman Coulter, "Anti-Streptolysin O (ASO)," retrieved online: https://www.beckmancoulter.com/wsrportal/techdocs?docname=/cisBAOSR6x94/%25%25/EN_ANTI-STREPOLYSIN.pdf, 2009.
Office Action dated Sep. 18, 2014 in U.S. Appl. No. 13/718,288.
Office Action dated Mar. 12, 2015 in U.S. Appl. No. 13/718,288.
Office Action dated Oct. 15, 2015 in U.S. Appl. No. 13/718,288.
Office Action dated Feb. 12, 2016 in U.S. Appl. No. 13/718,288.
Office Action dated Sep. 28, 2017, in U.S. Appl. No. 15/157,949.
Office Action dated Jun. 5, 2018, in U.S. Appl. No. 15/157,949.
Kiessling, Pediatrics, 1993, 92(1):39-43.
Korfei et al., Journal of Neuroimmunology, Dec. 2005, vol. 170, Issues 1-2.
Carpentier et al., Neurology, Aug. 2001, 57.
Nayeux et al., Biomarkers: Potential Uses and Limitations, NeuroRx, 2004, 1:182-188.
Wieslab, Guide to Autoimmune testing 2010, see p. 75, retrieved from URL: www.eurodiagnostica.com/upload/files/fileLibrary/metodhandbok-en-inl-18.pdf.).
Posner et al., Ann. NY Acad. Sci., 2006, 998:178-186.
Grauss et al., Neurol. Neurosurg. Psychiatry, 2004, 75:1135-1140.
Gorker et al., Balkan Med. J., 2011, 28:440-444.
Snider et al., Molecular Psychiatry, 2004, 9:900-907.
Kazarian et al., Journal of Neuroimmunology, 2009, 217:38-45.
Euroimmun. 2010, retrieved from URL: www.euroimmun.ch/uploads/media/FA_1111_I_UK_A09_.pdf.
Akinwusi et al., International Journal of General Medicine, "The new face of rheumatic heart disease in South West Nigeria," 2013:6 375-381.
Arain et al., Neuropsychiatric Disease and Treatment, "Maturation of the adolescent brain," 2013:9 449-461.
Armangue et al., J Child Neurol, "Autoimmune Encephalitis in Children," 2012 27:1460.
Church et al., J Neurol Neurosurg Psychiatry, "Tourette's syndrome: a cross sectional study to examine the PANDAS hypothesis," 2003; 74:602-607.
Coghlan et al., Neuroscience and Biobehavioral Reviews, "GABA system dysfunction in autism and related disorders: From synapse to symptoms," 2012.
Hoekstra et al., Molecular Psychiatry, "Is Tourette's syndrome an autoimmune disease?" (2002) 7, 437-445.
Kidd et al., Alternative Medicine Review, "Autism, An Extreme Challenge to Integrative Medicine. Part II Medical Management," vol. 7, No. 6, 2002.

(Continued)

*Primary Examiner* — Ellen J Marcsisin
(74) *Attorney, Agent, or Firm* — Foley & Lardner LLP

(57) ABSTRACT

Provided are methods for diagnosing a disease in a subject with a previous streptococcal infection by determining the presence or absence of one or more autoantibodies in a biological sample from the subject, wherein the one or more autoantibodies recognize an antigen from a protein selected from the group consisting of ELAVL2, ELAVL3, ELAVL4, Nova-1, Nova-2, Cdr1, Cdr2; and Cdr3. The presence of such autoantibodies is indicative of a positive diagosis for a post-streptococcal disease such as PANDAS, post-GABHS glomerulonephritis, rheumatic fever, autism and Syndenham's chorea.

7 Claims, No Drawings

(56) References Cited

PUBLICATIONS

Kirvan et al., Autoimmunity, "Streptococcal mimicry and antibody-mediated cell signaling in the pathogenesis of Sydenham's chorea," Feb. 23, 2007.
Kirvan et al., Journal of Neuroimmunology, "Antibody-mediated neuronal cell signaling in behavior and movement disorders," 2006.
Kirvan et al., Nature Medicine, "Mimicry and autoantibody-mediated neuronal cell signaling in Sydenham chorea," vol. 9, No. 7, Jul. 2003.
Kurlan et al., Pediatrics, The Pediatric Autoimmune Neuropsychiatric Disorders Associated With Streptococcal Infection (PANDAS) Etiology for Tics and Obsessive-Compulsive Symptoms: Hypothesis or Entity? Practical Considerations for the Clinician, 2004; 113; 883-886.
Murphy et al., Arch Pediatr Adolesc Med/vol. 156, "Prospective Identification and Treatment of Children With Pediatric Autoimmune Neuropsychiatric Disorder Associated With Group A Streptococcal Infection (PANDAS)," Apr. 2002 p. 356-361.
Murphy et al., Department of Psychiatry, University of Florida, "Preclinical/Clinical Evidence of Central Nervous System Infectious Etiology in PANDAS," p. 148-158.
Murphy et al., Psychiatr Clin N Am, "Immunology of Obsessive-Compulsive Disorder," 29 (2006) 445-469.
National Institute of Mental Health, "PANDAS studies are no longer recruiting patients," 2006, retrieved from URL: C:\Users\25396\AppData\Local\Microsoft\Windows\INetCache\Content.Outlook\PX0QFSXV\PANDAS Information (002).htm, (4 pages).
Neale, MedPage Today, "Autism Rate Climbs Again," Mar. 29, 2012, (2 pages).
O'Roak et al., Science, "Multiplex Targeted Sequencing Identifies Recurrently Mutated Genes in Autism Spectrum Disorders," vol. 338, Dec. 21, 2012.
Rhee et al., International Journal of General Medicine, "Lyme disease and pediatric autoimmune neuropsychiatric disorders associated with streptococcal infections (PANDAS): an overview," 2012:5 163-174.
Sacre et al., La Presse Medicale, Acute psychosis in anti-NMDA-receptor encephalitis, Sep. 2011, pp. 882-884.
Somnier, Department of Clinical Biochemistry, Immunology and Genetics, Staten's Serum Institute, "Autoimmune encephalitis—History and current knowledge," Nov. 30, 2012, (40 pages).
Somnier, Department of Clinical Biochemistry, Immunology and Genetics, Staten's Serum Institute, "Autoimmune encephalitis-Dopamine (post-streptococcal) related autoimmune encephalitis," Jun. 18, 2013, (11 pages).
Swedo et al., Pediatr Therapeut, From Research Subgroup to Clinical Syndrome: Modifying the PANDAS Criteria to Describe PANS (Pediatric Acute-onset Neuropsychiatric Syndrome), 2012, 2:2.
Vincent et al., Epilepsia, "Potentially pathogenic autoantibodies associated with epilepsy and encephalitis in children and adults," 52(Suppl.8)8-11, 2011.
Frederique Beaudonnet, "Anti-NMDA receptor encephalitis: An underestimated cause of acute psychiatric syndrome in children and young adults," La Presse Medical, Mar. 2012, 41:318-320, with partial English translation.

* cited by examiner

METHOD OF DETECTING ANTI-RI IN A SUBJECT WITH A PREVIOUS STREPTOCOCCAL INFECTION

CROSS-REFERENCE TO RELATED APPLICATIONS

This application is a Continuation of U.S. application Ser. No. 15/157,949, filed May 18, 2016, which is a Continuation of U.S. application Ser. No. 13/718,288, filed Dec. 18, 2012, which claims priority to U.S. Provisional Application No. 61/579,546, filed Dec. 22, 2011.

FIELD OF THE INVENTION

The invention relates to medically useful assays and methods for the diagnosis of post-streptococcal infection complications including PANDAS, post-GABHS glomerulonephritis, rheumatic fever, and Syndenham's chorea

BACKGROUND OF THE INVENTION

Pediatric Autoimmune Neuropsychiatric Disorder Associated with group A Streptococcal infection (PANDAS) is characterized by pediatric onset; neuropsychiatric disorders (obsessive compulsive disorder [OCD]) and/or tic disorder; abrupt onset and/or episodic course of symptoms; association with group A hemolytic streptococcal (GABHS) infection; and association with neurological abnormalities (motor hyperactivity or adventitious movements, including choreiform movements or tics). PANDAS is one of a spectrum of post-streptococcal infection complications that include post-GABHS glomerulonephritis, rheumatic fever, and Syndenham's chorea.

According to the National Institute of Mental Health (NIMH), children with PANDAS are clinically identified by certain criteria. These criteria include: (1) presence of obsessive-compulsive disorder and/or a tic disorder; (2) pediatric onset of symptoms (age 3 years to puberty); (3) episodic course of symptom severity; (4) association with group A streptococcal infection; and (5) association with neurological abnormalities (motoric hyperactivity, or adventitious movements, such as choreiform movements).

The children usually have dramatic, "overnight" onset of symptoms, including motor or vocal tics, obsessions, and/or compulsions. Some studies have shown no acute exacerbations associated with streptococcal infections among clinically defined PANDAS subjects while others have shown a profound one.

In addition to an OCD or tic disorder diagnosis, children may have other symptoms associated with exacerbations such as emotional lability, enuresis, anxiety, and deterioration in handwriting. Because the molecular mechanisms underlying the disease are largely unknown, there is no clear diagnostic test for these diseases. Thus, there is a need in the art for methods and assays capable of diagnosing PANDAS and other post-streptococcal infection complications.

SUMMARY OF THE INVENTION

The instant invention is based on the discovery that an immune reaction to a streptococcal infection can result in the production of autoantibodies capable of reacting with neuronal cells and inducing a pathological condition.

In a first aspect, the invention provides a method for diagnosing a disease in a subject, said method comprising, (a) determining the presence or absence of one or more autoantibodies in a biological sample from the subject with a previous Streptococcal infection, wherein the one or more autoantibodies recognize an antigen from a protein selected from the group consisting of ELAVL2, ELAVL3, ELAVL4, Nova-1, Nova-2, Cdr1, Cdr2 and Cdr3.

(b) identifying the subject as having a disease selected from the group consisting of PANDAS, post-GABHS glomerulonephritis, rheumatic fever, autism spectrum disorders and Syndenham's chorea, when the presence of one or more autoantibodies is detected, and identifying the subject as not having one of said diseases caused by the Streptococcal infection when said autoantibodies are absent.

In another aspect, the invention provides for a method comprising:

(a) testing a biological sample from a subject for the presence of a marker of a streptococcal infection; and (b) testing the biological sample for the presence or absence of one or more autoantibodies that recognize an antigen from a protein selected from the group consisting of ELAVL2, ELAVL3, ELAVL4, Nova-1, Nova-2, Cdr1, Cdr2 and Cdr3.

In yet another aspect, there is provided a method comprising:

(a) testing a biological sample from a subject for the presence of a marker of a streptococcal infection; and (b) testing the reactivity of one or more autoantibodies in the sample to neuronal cells wherein the one or more autoantibodies recognize an antigen from a protein selected from the group consisting of ELAVL2, ELAVL3, ELAVL4, Nova-1, Nova-2, Cdr1, Cdr2 and Cdr3.

In one embodiment of the above aspects, testing a biological sample from a subject for the presence of a marker of a streptococcal infection comprises determining the presence or absence of one or more anti-streptococcal antibodies. As used herein, the terms "antibody," "antibodies," "autoantibody," and "autoantibodies" includes whole antibodies and any antigen binding fragment or a single chain thereof. Thus the term "antibody" includes any protein or peptide containing molecule that comprises at least a portion of an immunoglobulin molecule. The terms "antibody," "antibodies," "autoantibody," and "autoantibodies" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-Ri, anti-Yo, and anti-Hu, for example, refers to a monoclonal or polyclonal antibody that binds and/or has an affinity to a particular antigen. For example, "anti-Hu" refers to an antibody that binds to the Hu antigen. The antibodies can be polyclonal, monoclonal, multispecific (e.g., bispecific antibodies), and antibody fragments, so long as they exhibit the desired biological activity.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., allergens.

The antibodies recognize antigens in proteins specific for the infectious agent and can be detected after the infectious agent has been cleared from the body. Therefore, the detection of an antibody that recognizes at least a portion of a protein from an infectious agent is an indication of a current or past infection. In this case, the detection of antibodies that specifically recognize antigens from streptococcal proteins can be used as a marker for a current or past streptococcal infection. In some embodiments of the above aspects, the anti-streptococcal antibody is selected from the group consisting of anti-streptolysin O, anti-deoxyribonuclease-B, anti-hyaluronidase, anti-nicotinamide adenine dinucleotidase and anti-streptokinase antibodies. In a related embodiment, the anti-streptococcal antibody is an anti-streptolysin O antibody.

Methods and assays described herein are directed to the detection of autoantibodies produced as a result of a streptococcal infection. Autoantibodies following a streptococcal infection can either be anti-streptococcal antibodies that cross-react with neurological structures and recognize an antigen from a protein in a subject or non-streptococcal antibodies arising as a result of the streptococcal infection that recognize proteins in the subject. The autoantibodies detected by methods and assays described herein recognize an antigen from a protein selected from the group consisting of ELAVL2, ELAVL3, ELAVL4, Nova-1, Nova-2, Cdr1, Cdr2 and Cdr3. The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

In one embodiment of the above aspects of the invention, the protein is selected from the group consisting of ELAVL2, ELAVL3, and ELAVL4. In a related embodiment, the autoantibody is anti-Hu. The Embryonic Lethal Abnormal Vision, *Drosophila*-Like protein (ELAVL) refers to a family of RNA-binding proteins also called the Hu family of proteins. These proteins are well known, have multiple isoforms, and can be further described by Genbank Accession numbers. For example, Genbank Accession Nos. CAI13377.1, CAI13376.1, CAC22160.1, AAH30692.1, EAW58586.1, EAW58585.1, EAW58584.1, EAW58583.1, EAW58582.1, EAW58581.1, NP_001164668.1, NP_001164666.1, NP_004423.2, CA113378.1, and Q9NZI8.2 are associated with the human ELAVL2 protein. Genbank Accession Nos. AAH11875.1, NP_115657.2, NP_001411.2, Q14576.3, AAK67714.1, AAK57545.1, EAW84221.1, and EAW84220.1 are associated with the human ELAVL3 protein. Genbank Accession Nos. CAI15793.1, CAI15792.1, CAI15791.1, CAI15790.1, CAI15789.1, CAI15788.1, CA114639.1, CAI14638.1, CAI14637.1, CAI14636.1, AAH36071.1, NP_001138249.1, NP_001138247.1, NP_068771.2, NP_001138246.1, NP_001138248.1, P26378.2, EAX06845.1, EAX06844.1, EAX06843.1, EAX06842.1, EAX06841.1, CAI14635.1, and CAI14634.1 are associated with the human ELAVL4 protein. Each of these Genbank sequences are herein incorporated by reference in their entirety.

In another embodiment of the above aspects of the invention, the protein is selected from the group consisting of Nova-1 and Nova-2. In a related embodiment, the autoantibody is anti-Ri. The Nova proteins are neuronal RNA binding proteins. These proteins are further described by GenBank Accession Nos. NP_002506.2, NP_006480.2, and NP_006482.1 for the human Nova-1 protein and 1DTJ_D, 1DTJ_C, 1DTJ_B, 1DTJ_A, Q9UNW9.1, 1EC6_B, 1EC6_A, NP_002507.1, AAC72355.1, and AAD13116.1 for the human Nova-2 protein. Each of these Genbank sequences are herein incorporated by reference in their entirety.

In yet another embodiment of the above aspects of the invention, the protein is selected from the group consisting of Cdr1, Cdr2 and Cdr3. In a related embodiment, the autoantibody is anti-Yo. Cdr1, 2, and 3 refer to Cerebellar Degeneration Related protein 1, 2, and 3. These proteins are further described by GenBank Accession Nos. NP_004056.2, P51861.2, AAI13475.1, AAI13473.1, and CAI42370.1 for the human Cdr1 protein; NP_001793.1, Q01850.2, AAA51961.1, AAH17503.2, EAW50610.1, and EAW50609.1 for the human Cdr2 protein. Each of these Genbank sequences is herein incorporated by reference in their entirety.

The term "biological sample" as used herein refers to any fluid or solid sample from the body of an animal. Examples of biological samples include but are not limited to plasma, serum, blood, lymphatic fluid, cerebrospinal fluid, synovial fluid, urine, saliva, mucous, phlegm and sputum. In one embodiment, the biological sample is selected from the group consisting of blood, serum, and plasma. In another embodiment, the biological sample is a human sample. A biological sample of the present invention may be collected by any suitable method. The biological sample may be used immediately or may be stored for later use. Any suitable storage method known in the art may be used to store the biological sample; for example the sample may be frozen at about −20° C. to about −70° C.

The term "diagnose" as used herein refers to the act or process of identifying or determining a disease or condition in a mammal or the cause of a disease or condition by the evaluation of the signs and symptoms of the disease or disorder. Usually, a diagnosis of a disease or disorder is based on the evaluation of one or more clinical factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

Unless defined otherwise, all technical and scientific terms used herein have the same meanings as commonly understood by one of ordinary skill in the art to which this invention belongs.

DETAILED DESCRIPTION OF THE INVENTION

Pediatric Autoimmune Neuropsychiatric Disorder Associated with group A Streptococcal infection (PANDAS) and other post-streptococcal infection complications can occur in subjects, typically children or young adults, after a streptococcal infection. Without being limited to a particular theory, autoantibodies produced during the immune reaction to the infection may contribute to the pathogenesis of the disease. Autoantibodies developing following a streptococcal infection, either anti-streptococcal antibodies that cross-react with neurological structures or non-streptococcal antibodies arising as a result of the streptococcal infection that recognize neuronal structures, may cause behavioral changes such as excessive compulsive disorders, tics, abnormal movements, or autism spectrum disorder symptoms.

These disorders are typically difficult to diagnose due to the lack of consistent biological markers found in subjects with these diseases. Assays and methods described herein can be used to detect biological markers present in subjects displaying abnormal behaviors following a streptococcal infection.

Sample Preparation

Provided herein are methods of using the information obtained through analysis of the presence or absence of one or autoantibodies in test samples of acellular biological sample or cell-containing samples. Test samples may be obtained from an individual or patient. Methods of obtaining test samples are well-known to those of skill in the art and include, but are not limited to, aspirations or drawing of blood or other fluids. Samples may include, but are not limited to, whole blood, serum, plasma, saliva, cerebrospinal fluid (CSF), pericardial fluid, pleural fluid, urine, and eye fluid.

In embodiments in which the presence or absence of an autoantibody will be determined using an acellular body fluid, the test sample obtained from a person may be a cell-containing liquid or an acellular body fluid (e.g., plasma or serum). In some embodiments in which the test sample contains cells, the cells may be removed from the liquid portion of the sample by methods known in the art (e.g., centrifugation) to yield acellular body fluid for the determination of the presence or absence of certain autoantibodies.

In other embodiments, the presence or absence of an autoantibody can be determined using a cell-containing sample. In these embodiments the cell-containing sample includes, but is not limited to, blood, urine, organ, and tissue samples. Cell lysis may be accomplished by standard procedures. In certain preferred embodiments, the cell-containing sample is a whole blood cell lysate. In certain other embodiments, the cell-containing sample is a white blood cell lysate. Methods for obtaining white blood cells from blood are known in the art (Rickwood et al., Anal. Biochem. 123:23-31 (1982); Fotino et al., Ann. Clin. Lab. Sci. 1:131 (1971)). Commercial products useful for cell separation include without limitation Ficoll-Paque (Pharmacia Biotech) and NycoPrep (Nycomed).

Identifying the Presence of a Current or Prior Streptococcal Infection

Group A *Streptococcus* (GAS) is a gram-positive bacterial genus composed of *Streptococcus pyogenes* strains. Group A *Streptococcus* strains have a surface antigen recognized by Lancefield serogrouping tests, termed the Lancefield Group A antigen. Lancefield groups (there are about 18 Lancefield groups) are composed of different *Streptococcus* species groups that have specific antigens and are distinguished by specific Lancefield antibody tests. In addition, group A *Streptococcus* strains are beta hemolytic meaning that the bacteria lyse red blood cells suspended in agar plates with secreted substances. These tests are frequently used to distinguish group A *Streptococcus* bacteria from group B and other *Streptococcus* groups. These organisms appear as pairs and chains when gram-stained. Although these bacteria can harmlessly colonize people on their throat and skin, sometimes they can cause mild to serious diseases. *Streptococcus* bacteria have many components that contribute to the pathogens' ability to cause disease:

Lipoteichoic acid on its surface helps the bacteria to bind to epithelial cell membranes;

M proteins (over 100 types on the GAS bacterial strains) help the bacteria resist immunologic host defenses;

Exotoxins, nucleases and enzymes, for example, DNAses A, C and D, streptolysin S, proteinase, streptokinase, and pyrogenic exotoxins (A-D);

Human immune system stimulators; for example, streptolysin O, DNAse B, and hyaluronidase;

Capsular polysaccharide (C-substance) composed of a branched polymer of L-rhamnose and N-acetyl-D-glucosamine may have a role in increased invasive capacity;

C5A peptidase destroys the chemotactic signals by cleaving the complement component of C5A.

Exotoxins cause the scarlet fever rash, damage organs, may cause shock, and inhibit the human immune system. The M protein, a major virulence factor, is a macromolecule incorporated in fimbriae present on the cell membrane projecting on the bacterial cell wall. More than fifty types of Streptococcus pyogenes M proteins have been identified based on antigenic specificity, and the M protein is the major cause of antigenic shift and antigenic drift among GAS. The M protein binds the host fibrinogen and blocks the binding of complement to the underlying peptidoglycan. This allows survival of the organism by inhibiting phagocytosis. Strains that contain an abundance of M protein resist phagocytosis, multiply rapidly in human tissues, and initiate disease process. After an acute infection, type-specific antibodies develop against M protein activity in some cases. R and T proteins are used as epidemiological markers, but have no known role in virulence. Detection of any protein or antibody produced as a result of or from a streptococcal infection can be used as a marker to determine the existence of a past or current streptococcal infection.

Methods and assays described herein describe the testing of a biological sample for the presence of a marker of a streptococcal infection. The marker can indicate a live bacterial infection or the presence of a past infection. The term "live bacterial infection" is intended to mean a bacterial infection that is still present in the subject. Past streptococcal infections can be diagnosed by determining the presence or absence of a marker of a streptococcal infection that remains after the bacteria have been cleared from the body. A live streptococcal infection or the existence of a past streptococcal infection can be diagnosed by a variety of methods known in the art. For example, after a history and physical examination, many clinicians presumptively diagnose strep throat from its symptom production and throat appearance. A streptococcal infection can also be diagnosed from cultures of the throat or other site of infection. Cultures can be tested on blood agar plates that contain two different antibiotics and cause beta hemolysis (complete blood red cell lysis to form a clear area) of the red blood cells. In addition, there are rapid tests (RADT or rapid antigen detection test) that take only a few minutes to complete that detect a group A carbohydrate surface antigen produced by the streptococcal bacteria, with specificity of about 95% or better and fairly good sensitivity of about 80%-90%.

A streptococcal infection can also be diagnosed by testing for the presence or absence of streptococcal antibodies in a biological sample. Suitable biophysical or biomolecular detection methods for qualitatively detecting an antibody comprise any suitable method known in the art. Such methods include, without being limited thereto, methods as applied for qualitative or quantitative assays such as, for example, Enzyme-linked Immunosorbent Assay (ELISA), ELISPOT-Assay, Western-Blot or Immunoassays. In one embodiment, the presence or absence of an antibody selected from the group consisting of anti-streptolysin O, anti-deoxyribonuclease-B, anti-hyaluronidase, anti-nicotinamide adenine dinucleotidase and anti-streptokinase is determined. In some instances, it may be more desirable to test for the presence of more than one antibody to confirm the presence or past existence of a streptococcal infection in the subject. In one embodiment, the presence or absence of anti-streptolysin O is used as a marker to test for a current or past streptococcal infection. Detection of antibodies as described herein can also be determined by methods the same as those used for the characterization of autoantibodies in a sample in foregoing descriptions.

Characterization of Autoantibodies in a Sample

Autoantibodies and/or antibodies can be detected in a sample by a variety of known methods. As described previously, these methods include, for example, Enzyme-linked Immunosorbent Assay (ELISA), ELISPOT-Assay, Western-Blot or Immunoassays. Such methods may comprise optical, radioactive, chromatographic methods, fluorescence detection methods, radioactivity detection methods, Coomassie-Blue staining, Silver staining or other protein staining methods, electron microscopy methods, methods for staining tissue sections by immunohistochemistry or by direct or indirect immunofluorescence, etc. Such methods may be applied either with the autoantibody or may involve the use of further tools, for example, the use of a secondary antibody, specifically binding to the constant part of the autoantibody. The secondary antibody may be labeled to allow a specific detection of the secondary antibody.

Immunoassays, such as an ELISA are commonly used for the detection of antibodies in a biological sample. In one example of an ELISA, the antibodies or antigens are immobilized on a selected surface, such as a well in a polystyrene microtiter plate, dipstick, or column support. Then, a test composition suspected of containing the desired antigen or antibody, such as a biological sample, is added to the wells. After binding and washing to remove non specifically bound immune complexes, the bound antigen or antibody may be detected. Detection is generally achieved by the addition of another antibody, specific for the desired antigen or antibody that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label. Variations on ELISA techniques are known to those of skill in the art.

As used herein, the term "label" intends a directly or indirectly detectable compound or composition that is conjugated directly or indirectly to the composition to be detected, for example, N-terminal histadine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described in, for example, Haugland, Richard P. (1996) Handbook of Fluorescent Probes and Research Chemicals ($6^{th}$ ed.). Examples of luminescent probes include, but are not limited to, aequorin and luciferases.

Competition ELISAs are assays in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In the method of the present invention for detecting the presence of at least one antibody against one of the above defined autoantigens or antigens in a sample a qualitative or a quantitative determination can be carried out. "Qualitative determination" in the context of the inventive method is to be understood as any method for specifically identifying the presence of a specific autoantibody, for example, an autoantibody directed against one or more of specific proteins selected from the autoantigenic proteins ELAVL2, ELAVL3, ELAVL4, Nova-1, Nova-2, Cdr1, Cdr2 and Cdr3, or a fragment, variant or epitope thereof "Quantitative determination" in the context of the inventive method is to be understood as any method for determination of an antibody or (antibody) proteins or peptides, protein fragments, variants or epitopes thereof, known by a skilled person suitable for quantifying the amount of a autoantibody or a secondary antibody, in a sample. As an example, the inventive method may be carried out with a test sample as a concurrent standard, containing a defined amount of an autoantibody against at least one of the above autoantigenic proteins, and in parallel with a second sample, which is derived from a patient and contains an unknown amount of an autoantibody to be determined against at least one of the above autoantigenic proteins. A comparison of the defined amount of the autoantibody in the test sample with the amount of the autoantibody in the second sample will allow a precise determination of the amount of autoantibody in the second sample. A concurrent standard may be applied either parallel to carrying out the inventive method or, for example, prior to said method, by preparing a standard curve, which may be used in the subsequent quantification.

Testing the Reactivity of Autoantibodies to Neuronal Cells

Autoantibodies produced in an immune response to a streptococcal infection can be specific to proteins described herein or can cross-react to the proteins described herein, for example, a protein selected from the group consisting of ELAVL2, ELAVL3, ELAVL4, Nova-1, Nova-2, Cdr1, Cdr2 and Cdr3. These proteins can be expressed endogenously in neuronal cells and can cross-react with autoantibodies produced from a streptococcal infection. The term "react" in this sense is intended to describe the binding of the autoantibody to a neuronal cell, structure, nucleic acid, nucleoprotein, or protein. Such reactivity can be detected by a variety of common methods.

In one embodiment, the reactivity of an autoantibody to a neuronal cell can be determined by immunoassays. In a related embodiment, the immunoassay is an immunofluorescence assay. In a further embodiment, the immunofluorescence assay is an indirect immunofluorescence assay. Immunofluorescence is a technique used for light microscopy with a fluorescence microscope and is used primarily on biological samples. This technique uses the reactivity of antibodies to their antigen to target fluorescent dyes to specific biomolecule targets within a cell, and therefore allows visualization of the distribution of the target molecule through the sample. Immunofluorescence is a widely used example of immunostaining and is a specific example of immunohistochemistry that makes use of fluorophores to visualize the location of the antibodies.

Immunofluorescence can be used on tissue sections, cultured cell lines, or individual cells, and may be used to analyze the distribution of proteins, glycans, small biological and non-biological molecules, and the reactivity of antibodies in a biological sample to cells. Immunofluorescence can be used in combination with other, non-antibody methods of fluorescent staining, for example, use of DAPI to label DNA or Evans blue stain to label cells. Several microscope designs can be used for analysis of immunofluorescence samples; the simplest is the epifluorescence microscope, and the confocal microscope is also widely used. Various super-resolution microscope designs that are capable of much higher resolution can also be used.

Primary, or direct, immunofluorescence uses a single antibody that is chemically linked to a fluorophore. The antibody recognizes the target molecule and binds to it, and the fluorophore it carries can be detected via microscopy.

Secondary, or indirect, immunofluorescence uses two antibodies; the unlabeled first (primary) antibody specifically binds the target molecule, and the secondary antibody, which carries the fluorophore, recognizes the primary antibody and binds to it. Multiple secondary antibodies can bind a single primary antibody. This provides signal amplification by increasing the number of fluorophore molecules per antigen.

This protocol is possible because an antibody consists of two parts, a variable region (which recognizes the antigen) and constant region (which makes up the structure of the antibody molecule). It is important to realize that this division is artificial and in reality the antibody molecule is four polypeptide chains: two heavy chains and two light chains. Various primary antibodies can recognize various antigens (have different variable regions), but all share the same constant region. All these antibodies may therefore be recognized by a single secondary antibody.

Different primary antibodies with different constant regions are typically generated by raising the antibody in different species. For example, a researcher might create primary antibodies in a goat that recognize several antigens, and then employ dye-coupled rabbit secondary antibodies that recognize the goat antibody constant region ("rabbit anti-goat" antibodies). The researcher may then create a second set of primary antibodies in a mouse that could be recognized by a separate "goat anti-mouse" secondary antibody. This allows re-use of the difficult-to-make dye-coupled antibodies in multiple experiments.

In some instances, the reactivity of an autoantibody with a neuronal cell can be detected by a physical change in the neuronal cells. In one embodiment, this physical change is neurite retraction. In a neurite retraction assay, the change in the length of neurites of neuronal cells can be determined after addition of a biological sample with autoantibodies. A decrease in the length of neurites after the administration of an autoantibody is an indication of reactivity of the autoantibody to the neuronal cell. This assay is typically performed on neuronal cells growing in a cell culture environment. Techniques for culturing and differentiating neuronal cells are known in the art.

Diagnosis of Disease

Provided herein are methods and assays for the diagnosis of certain disease that can occur following a group A streptococcal infection. By way of example, these diseases include PANDAS, post-GABHS glomerulonephritis, rheumatic fever, Syndenham's chorea, autism spectrum disorder, obsessive-compulsive disorder, Tourette syndrome, and tic disorders. These disorders usually occur in children and can also be associated with exacerbations such as emotional lability, enuresis, anxiety, and deterioration in handwriting. In one embodiment of the aspects described herein, the disease is PANDAS.

Example 1

Hu, Ri, and Yo Antibody Immunofluorescence Assay

Biological samples can first be obtained and tested for anti-streptococcal antibodies such as anti-streptolysin O. Eighty anti-streptolysin O (ASO) positive serum samples, 30 ASO negative serum samples, and ten normal serum samples were obtained. For the determination of ASO positive or negative, an antibody quality of 200 IU/ml was used. Samples were submitted for ASO testing without clinical information and used after de-identification.

1:40 dilutions of the patient sera was prepared in a pH buffered solution. Slides with monkey cerebellar tissues affixed thereto were removed from cold storage and kept at room temperature for five minutes. Approximately 50 µl of diluted sera and controls were applied to the reaction wells on the slides. The controls consisted of samples with antibodies determined to have reactivity to one or all of the Hu, Yo, and Ri antigens. The slides were incubated for 30 minutes at room temperature in a humidity chamber. Next, the slides were rinsed in a pH-buffered solution and placed in a washing dish with the pH-buffered solution for two minutes. The slides were then removed from the washing dish and the edges of the slides were blotted with a paper towel. Approximately one drop of a diluted secondary conjugate was then added to each well. The slides were incubated at room temperature for 30 minutes in a humidity chamber. Next the slides were rinsed with a pH-buffered solution and placed in a washing dish filled with the pH-buffered solution and one drop of Evans blue stain. The slides were incubated in this solution for 2-5 minutes and then washed with fresh pH-buffered solution.

Twelve samples showed fluorescence in IFA up to at least 1:160 titer. These samples were then tested in Euroimmune Anti-Neuronal Antigens Westernblot (IgG) assay, along with four samples that were negative in the immunofluorescence assay. These results are depicted in the following table.

| Sample | ASO Result (200 IU/ml cutoff) | ASO Value (IU/ml) | IFA Result (1:40 screen) | Western Blot Ri, 80 kDa | Yo, 62 kDa | Ri, 55 kDa | Hu, 38 kDa | Yo, 34 kDa |
|---|---|---|---|---|---|---|---|---|
| A | NT (Normal) | n/a | + (1:320) | | | | | |
| B | − | 49 | + (1:160) | | | | + | |
| C | + | 265 | + (1:320) | | | | | |
| D | + | 331 | + (1:160) | | | | | |
| E | + | 778 | + (1:320) | + | + | | | + |
| F | − | 65 | + (1:160) | | | | + | |
| G | + | 213 | + (1:160) | + | | | | |
| H | − | 21 | + (1:160) | | | | | |
| I | + | 501 | + (1:320) | | | | | |
| J | + | 319 | + (1:160) | + | | | | |
| K | + | 262 | + (1:320) | + | + | | | + |
| L | − | 6 | + (1:160) | | | | | |
| M | + | 263 | − | | | | + | |
| N | + | 581 | − | | | | | |
| O | + | 441 | − | | | + | | |
| P | + | 498 | − | | | | | + |

The aforementioned assays and methods can be used to diagnose disease in a subject. A subject can be a mammal such as a human or laboratory research mammal such as a mouse, a rat, or a rabbit. In one embodiment, the subject is a human. The subject can also be a human patient under the care of a medical practitioner.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A detection method comprising:
    (a) obtaining a fluid sample from a subject previously diagnosed with a Streptococcal infection and suspected of having pediatric autoimmune neuropsychiatric disorder associated with group A (PANDAS);
    (b) testing the fluid sample for at least one anti-streptococcal antibody;
    (c) testing the fluid sample for one or more autoantibodies that recognize an antigen from a protein selected from the group consisting of neuro-oncological ventral antigen 1 (Nova-1) and neuro oncological ventral antigen 2 (Nova-2), wherein at least one autoantibody of the one or more autoantibodies is anti-Ri; and
    (d) detecting in the fluid sample obtained from the same subject the one or more anti-streptococcal antibodies and the one or more autoantibodies by an immunofluorescence assay.

2. The method of claim 1, wherein at least one anti-streptococcal antibody is an anti-streptolysin O (ASO) antibody.

3. The method of claim 1, wherein at least one additional autoantibody is selected from anti-Hu or anti-Yo.

4. The method of claim 1, wherein the protein is Nova-1.

5. The method of claim 1, wherein the subject is a human.

6. The method of claim 1, wherein the subject is a pediatric subject.

7. The method of claim 1, wherein the fluid sample is selected from the group consisting of blood, serum, and plasma.

* * * * *

UNITED STATES PATENT AND TRADEMARK OFFICE
CERTIFICATE OF CORRECTION

| | | |
|---|---|---|
| PATENT NO. | : 11,768,202 B2 | Page 1 of 1 |
| APPLICATION NO. | : 16/209100 | |
| DATED | : September 26, 2023 | |
| INVENTOR(S) | : Naides et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this
Thirty-first Day of December, 2024

Derrick Brent
*Acting Director of the United States Patent and Trademark Office*